United States Patent
Wünsch et al.

[11] Patent Number: 6,129,908
[45] Date of Patent: Oct. 10, 2000

[54] COSMETIC OR PHARMACEUTICAL PREPARATIONS COMPRISING 1,3,5-TRIAZINE DERIVATIVES AND ZINC OXIDE

[75] Inventors: Thomas Wünsch, Speyer; Horst Westenfelder, Neustadt, both of Germany

[73] Assignee: BASF Aktiengesellschaft, Ludwigshafen, Germany

[21] Appl. No.: 09/432,203

[22] Filed: Nov. 2, 1999

[30] Foreign Application Priority Data

Nov. 2, 1998 [DE] Germany ............ 198 50 364
Aug. 27, 1999 [DE] Germany ............ 199 40 889

[51] Int. Cl.[7] ............ A61K 7/42; A61K 7/44; A61K 7/00; A61K 31/53
[52] U.S. Cl. ............ 424/59; 424/60; 424/400; 424/401; 514/241
[58] Field of Search ............ 424/59, 60, 400, 424/401; 514/241

[56] References Cited

U.S. PATENT DOCUMENTS

| | | | |
|---|---|---|---|
| 4,514,231 | 4/1985 | Kerner et al. | 106/309 |
| 5,489,431 | 2/1996 | Ascione et al. | 424/401 |
| 5,643,557 | 7/1997 | Eteve et al. | 424/60 |
| 5,690,915 | 11/1997 | Eteve et al. | 424/60 |
| 5,690,917 | 11/1997 | Eteve et al. | 424/60 |
| 5,695,747 | 12/1997 | Forestier et al. | 424/59 |
| 5,725,844 | 3/1998 | Gers-Barlag et al. | 424/59 |
| 5,788,955 | 8/1998 | Eteve et al. | 424/60 |
| 5,795,565 | 8/1998 | Eteve et al. | 424/60 |
| 5,851,542 | 12/1998 | Gers-Barlag | 424/401 |
| 5,945,091 | 8/1999 | Habeck et al. | 424/59 |
| 5,961,960 | 10/1999 | Dilk et al. | 424/59 |
| 5,980,872 | 11/1999 | Luther et al. | 424/59 |
| 5,985,925 | 11/1999 | Josso et al. | 424/59 |

FOREIGN PATENT DOCUMENTS

| | | |
|---|---|---|
| 518772 | 12/1992 | European Pat. Off. . |
| 518773 | 12/1992 | European Pat. Off. . |
| 685223 | 12/1995 | European Pat. Off. . |
| 3314742 | 10/1984 | Germany . |
| 19602619 | 8/1997 | Germany . |
| 19632913 | 2/1998 | Germany . |
| 19633012 | 2/1998 | Germany . |
| 19635057 | 3/1998 | Germany . |
| 19703471 | 8/1998 | Germany . |

*Primary Examiner*—Shelley A. Dodson
*Attorney, Agent, or Firm*—Keil & Weinkauf

[57] ABSTRACT

Cosmetic or pharmaceutical preparations for protecting human skin or human hair from solar rays which contain
a) from 0.1 to 10% by weight of one or more 1,3,5-triazine derivatives of the formula I,

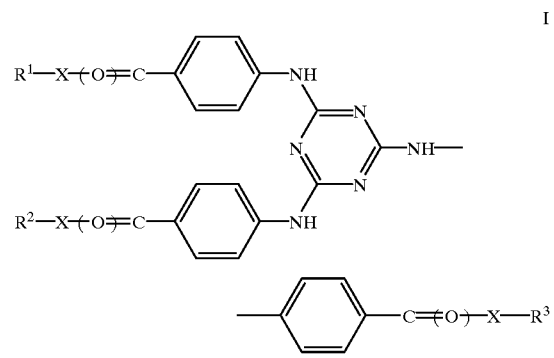

in which the substituents independently of one another have the following meanings:

$R^1$ to $R^3$ are $C_1$–$C_{20}$-alkyl, aryl, heteroaryl, optionally substituted;
X is O, $NR^4$;
$R^4$ is hydrogen, $C_1$–$C_{20}$-alkyl, aryl, heteroaryl, optionally substituted, and
b) from 0.1 to 15% by weight of zinc oxide.

7 Claims, No Drawings

COSMETIC OR PHARMACEUTICAL PREPARATIONS COMPRISING 1,3,5-TRIAZINE DERIVATIVES AND ZINC OXIDE

Cosmetic or pharmaceutical preparations comprising 1,3,5-triazine derivatives and zinc oxide.

The invention relates to cosmetic or pharmaceutical sunscreen preparations comprising 1,3,5-triazine derivatives and zinc oxide.

The sunscreens used in cosmetic and pharmaceutical preparations have the task of preventing or at least diminishing the extent of the harmful effects of sunlight on human skin. In addition, these sunscreens, however, also serve to protect other ingredients from decomposition or degradation by UV radiation. In hair cosmetic formulations, the intention is to prevent damage to the keratin fibers by UV rays.

The sunlight which reaches the earth's surface contains UV-B radiation (280 to 320 nm) and UV-A radiation (>320 nm), which directly border the visible light region. The effect on human skin is evident, particularly in the case of UV-B radiation, from sunburn. Accordingly, the industry offers a relatively large number of substances which absorb UV-B radiation and thus prevent sunburn.

An advantageous UV-B filter is 2,4,6-trianilino-p-(carbo-2'-ethylhexyl-1'-oxy)-1,3,5-triazine, which is marketed by BASF Aktiengesellschaft under the tradename Uvinul® T150.

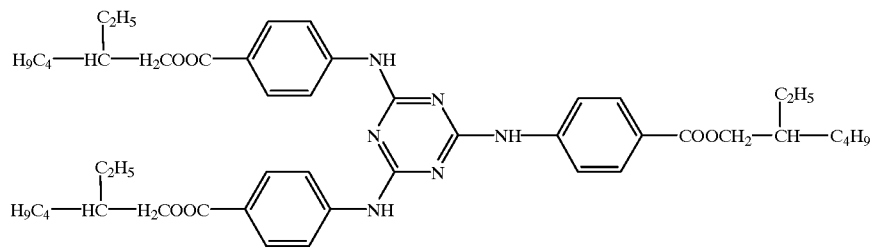

Uvinul® T150 is notable for good UV absorption properties and an extremely high absorbance coefficient of >1500 at 314 nm.

A disadvantage of this UV-B filter is, however, the inadequate solubility in cosmetic oils for many cosmetic applications.

Because it is possible to achieve only low use concentrations of Uvinul® T150, the use of this UV-B filter for the preparation of cosmetic and pharmaceutical sunscreen preparations with high sun protection factors (SPF>15) is often limited.

Many patent applications and patent specifications, including U.S. Pat. No. 5,489,431, DE-A-197 03 471, DE-A-196 32 913, DE-A-196 02 619, DE-A-196 35 057, DE-A-196 33 012, EP-A-0 685 223, describe the use of solubilizers, lipophilic solvents or specific combinations with other UV absorbers for improving the solubility of Uvinul® T150.

It is an object of the invention to provide cosmetic or pharmaceutical sunscreen preparations which have only low concentrations of UV absorbers but very high sun protection factors.

We have found that this object is achieved according to the invention by cosmetic or pharmaceutical preparations comprising
a) from 0.1 to 10% by weight of one or more 1,3,5-triazine derivatives of the formula I,

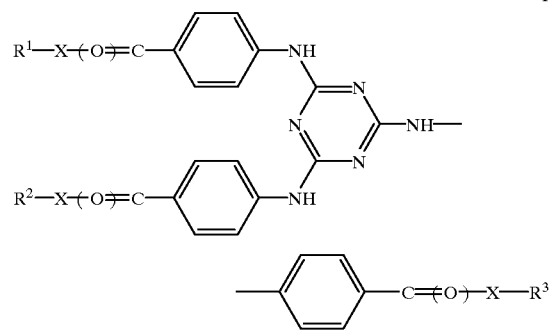

in which the substituents independently of one another have the following meanings:
$R^1$ to $R^3$
are $C_1$–$C_{20}$-alkyl, aryl, heteroaryl, optionally substituted;
X is O, $NR^4$;
$R^4$ is hydrogen, $C_1$–$C_{20}$-alkyl, aryl, heteroaryl, optionally substituted, and
b) from 0.1 to 15% by weight of zinc oxide.

Alkyl radicals $R^1$ to $R^4$ which may be mentioned are branched or unbranched $C_1$–$C_{20}$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives from the group of the above-mentioned alkyl radicals $R^1$ to $R^4$ are branched or unbranched $C_1$–$C_{12}$-alkyl chains, particularly preferably branched or unbranched $C_4$–$C_8$-alkyl chains, for example n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl.

Aryl is taken to mean aromatic rings or ring systems having from 6 to 18 carbon atoms in the ring system, for example phenyl or naphthyl, which can be optionally substituted by one or more radicals such as halogen, for example fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Preference is given to optionally substituted phenyl, methoxyphenyl and naphthyl.

Heteroaryl radicals are advantageously single or fused aromatic ring systems having one or more heteroaromatic 3- to 7-membered rings. Heteroatoms which may be present in the ring or ring system are one or more nitrogen, sulfur and/or oxygen atoms.

The zinc oxide used as inorganic pigment is preferably used as micropigment having a primary particle size of from 10 to 60 nm. In addition, it can be advantageous for the zinc oxide to be present in hydrophobicized form, i.e. to have been treated superficially to repel water. Examples of surface-treated pigments can be found inter alia in DE-A-33 14 742, EP-A-0 518 772 and in EP-A-0 518 773.

Preference is given to cosmetic or pharmaceutical preparations comprising
a) from 1 to 8% by weight of one or more 1,3,5-triazine derivatives of the formula I in which the substituents independently of one another have the following meanings:
$R^1$ to $R^3$
are $C_4$–$C_8$-alkyl;
X is O, $NR^4$;
$R^4$ is hydrogen, $C_4$–$C_8$-alkyl, and
b) from 0.1 to 10% by weight of zinc oxide.

Particular preference is given to cosmetic or pharmaceutical preparations comprising
a) from 2 to 6% by weight of 2,4,6-trianilino-p-(carbo-2'-ethylhexyl-1'-oxy)-1,3,5-triazine of the formula Ia

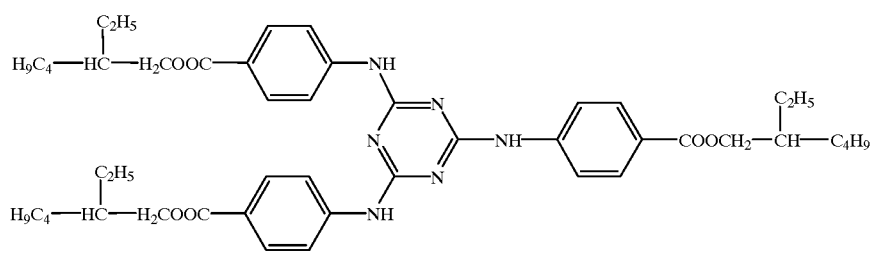

Ia and
b) from 2 to 8% by weight of zinc oxide.

Very particular preference is given to cosmetic or pharmaceutical preparations comprising
a) from 2.5 to 5% by weight of 2,4,6-trianilino-p-(carbo-2'-ethylhexyl-1'-oxy)-1,3,5-triazine of the formula Ia and
b) from 3.5 to 6% by weight of zinc oxide.

The cosmetic and pharmaceutical preparations comprising sunscreens are normally based on a carrier which comprises at least one oil phase. Accordingly, suitable preparations are oils, oil-in-water and water-in-oil emulsions, creams and pastes, lip-protection stick compositions or fat-free gels.

Such sunscreen preparations can accordingly be in liquid, paste or solid form, for example as water-in-oil creams, oil-in-water creams and lotions, aerosol foam creams, gels, oils, marking pencils, powders, sprays or alcoholic/aqueous lotions.

Examples of conventional oil components in cosmetics are liquid paraffin, glyceryl stearate, isopropyl myristate, diisopropyl adipate, cetylstearyl 2-ethylhexanoate, hydrogenated polyisobutene, vaseline, caprylic acid/capric acid triglycerides, microcrystalline wax, lanolin and stearic acid.

Examples of conventional cosmetic auxiliaries which may be suitable as additives are coemulsifiers, fats and waxes, stabilizers, thickeners, biogenic active ingredients, film formers, fragrances, dyes, lusterizing agents, preservatives, pigments, electrolytes (e.g. magnesium sulfate) and pH regulators. Suitable coemulsifiers are, preferably, known W/o and also O/W emulsifiers, such as polyglycerol esters, sorbitan esters or partially esterified glycerides. Typical examples of fats are glycerides; waxes which may be mentioned include beeswax, paraffin wax or microwaxes, optionally in combination with hydrophilic waxes. Stabilizers which may be used are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinyl pyrrolidone. Biogenic active ingredients are taken to mean, for example, plant extracts, protein hydrolysates and vitamin complexes. Examples of traditional film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Suitable preservatives are, for example, formaldehyde solution, parabens such as methylparaben, 1,2-dibromo-2,4-dicyanobutane, p-hydroxybenzoate or sorbic acid. Suitable lusterizing agents are, for example, glycol distearic esters, such as ethylene glycol distearate, but also fatty acids and fatty acid monoglycol esters. The dyes which may be used are those substances suitable and approved for cosmetic purposes, such as, for example, those listed in the publication Kosmetische Farbemittel from the Farbstoffkommission der Deutschen Forschungsgemeinschaft, published by Verlag Chemie, Weinheim, 1984. These dyes are normally used in concentrations of from 0.001 to 1% by weight, based on the total mixture.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the formulation. The formulations can be prepared in a manner known per se, i.e. for example by hot, cold, hot/cold or PIT emulsification. This is purely a mechanical process and there is no chemical reaction.

Finally, it is possible additionally to use further substances known per se which absorb in the UV region, provided they are stable in the overall system of the combination of UV filters to be used according to the invention.

UV filter substances which can be used with the novel combination of 1,3,5-triazine derivatives of the formula I and zinc oxide are any UV-A and UV-B filter substances. Examples which may be mentioned are:

TABLE 1

| No. | Substance | CAS No. (= acid) |
|---|---|---|
| 1 | 4-Aminobenzoic acid | 150-13-0 |
| 2 | 3-(4'-Trimethylammonium)benzylidene-2-bornanone methylsulfate [sic] | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane-sulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate [sic] | 71617-10-2 |
| 11 | 2-Ethylhexyl 4-methoxycinnamate | 5466-77-3 |
| 12 | 2-Hydroxy-4-methoxybenzophenone-5-sulfone [sic] (sulisobenzone) and the sodium salt | 4065-45-6 |
| 13 | 3-(4'-Methylbenzylidene)-2-bornanone | 36861-47-9 |
| 14 | 3-Benzylidene-2-bornanone | 15087-24-8 |
| 15 | 1-(4'-Isopropylphenyl)-3-phenyl-1,3-propanedione | 63260-25-9 |
| 16 | 4-Isopropylbenzyl salicylate | 94134-93-7 |
| 17 | 3-(4-Imidazolyl)acrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl o-aminobenzoate or 5-methyl-2-(1-methylethyl) 2-aminobenzoate [sic] | 134-09-8 |
| 21 | Glyceryl p-aminobenzoate or 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexenone) | 1641-17-4 |
| 24 | Triethanolamine salicylate | 2174-16-5 |
| 25 | Dimethoxyphenylglyoxalic acid or sodium 3,4-dimethoxyphenylglyoxalate | 4732-70-1 |
| 26 | 3-(4'-Sulfobenzylidene)-2-bornanone and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | Bis,bis(2-ethylhexyl) 4,4'-[[6-[[4-[[(1,1-dimethylethyl)amino]carbonyl]phenyl]amino]-1,3,5-triazine-2,4-diyl]diimino]benzoate | 154702-15-5 |
| 30 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |

TABLE 1-continued

| No. | Substance | CAS No. (= acid) |
|---|---|---|
| 31 | Dimethicone diethylbenzalmalonate | 207574-74-1 |
| 32 | Bis[2-hydroxy-5-tert-octyl-3-(benzotriazol-2-yl)phenyl]methane (bisoctyltriazone) | 103597-45-1 |
| 33 | 1H-Benzimidazole-4,6-disulfonic acid, 2,2'-(1,4-phenylene)bis-, disodium salt (benzimidazylate) | 180898-37-7 |
| 34 | Phenol, 2,2'-[6-(4-methoxyphenyl)-1,3,5-triazine-2,4-diyl]bis[5-[(2-ethylhexyl)oxy] (aniso triazine) | 187393-00-6 |

To protect human hair against UV rays, the novel sunscreen preparations can be used as shampoos, lotions, gels, hairsprays, aerosol foam creams or emulsions inter alia for washing, coloring and for styling the hair.

The UV filter action of the novel preparations can also be utilized for stabilizing active ingredients and auxiliaries in cosmetic and pharmaceutical formulations.

The novel preparations are notable for a particularly high absorptive power in the UV-B radiation region with a sharp band structure and high sun protection factors.

In particular, the high sun protection factor of the preparations, which was measured even at low concentrations of UV-absorbing active ingredients, was surprising.

Thus, the sun protection factor of the cosmetic or pharmaceutical formulations is in the range greater than 14, preferably in the range greater than 25. Corresponding values can be achieved, for example, using a sunscreen emulsion with a content of Uvinul® T150 of 3% by weight and a concentration of zinc oxide of 4% by weight. It is, however, also possible to achieve the abovementioned sun protection values by varying the use amounts of 1,3,5-triazine derivates of the formula I (in the range from 0.1 to 10% by weight) and zinc oxide (in the range from 0.1 to 10% by weight).

As can be seen from Table 2, the combination of Uvinul® T150 and zinc oxide (emulsion A) shows synergistic effects with regard to the sun protection factor, which clearly exceed the additive effects of the respective individual components (emulsion B and C). By contrast, the sun protection factor of a comparable Uvinul® T150/$TiO_2$-containing emulsion (emulsion D) is lower than the sum of the sun protection factors of the individual components (emulsion C and E).

TABLE 2

| Emulsion[1] | Uvinul ® T150 | $TiO_2$ | ZnO | Sun protection factor[2] |
|---|---|---|---|---|
| A | 3% by weight | — | 4% by weight | 30 |
| B | — | — | 4% by weight | 4 |
| C | 3% by weight | — | — | 9 |
| D | 3% by weight | 4% by weight | — | 11 |
| E | — | 4% by weight | — | 6 |

[1]Preparation, see Examples;
[2]Determined by the Colipa method, described in Parfuem. Kosmet. (1994), 75(12), 856

Another advantage of the novel preparations is the fact that satisfactory sun protection values can be obtained even using very small amounts of triazine derivatives of the formula I (from 0.1 to 1.5% by weight) and zinc oxide (likewise from 0.1 to 1.5% by weight).

The examples below serve to illustrate the present invention without limiting it.

General procedure for the preparation of the novel preparations as emulsions

The respective phases I and II were heated separately to about 85° C. Then, phase II was stirred into phase I with homogenization. After a short post-homogenization period, the emulsion was cooled to room temperature with stirring and transferred into containers. All amounts refer to the total weight of the preparations.

EXAMPLE 1

Emulsion A comprising 3% by weight of Uvinul® T150 and 4% by weight of zinc oxide (sun protection factor 30)

|   | %     | Raw material        | INCI                            |
|---|-------|---------------------|---------------------------------|
| I | 6.00  | Chremophor ® WO7    | PEG-7 Hydrogenated Castor Oil   |
|   | 0.30  | Chremophor ® RH 410 | PEG-40 Hydrogenated Castor Oil  |
|   | 2.00  | Elfacos ® ST9       | PEG-45/Dodecyl Glycol Copolymer |
|   | 2.00  | Elfacos ® C26       | Hydroxyoctacosanyl Hydroxystearate |
|   | 12.00 | Finsolv ® TN        | Alkyl Benzoate                  |
|   | 0.5   | Magnesium stearate  | Magnesium Stearate              |
|   | 0.5   | Aluminum stearate   | Aluminum Stearate               |
|   | 10.00 | Isopropyl myristate | Isopropyl Myristate             |
|   | 3.00  | Uvinul ® T150       | Octyl Triazone                  |
|   | 0.5   | Preservative        | Preservative                    |
|   | 5.0   | Witconol ® APM      | PPG-3 Myristyl Ether            |
|   | 4.0   | Zinc oxide          | Zinc Oxide                      |
| II| 0.3   | Preservative        | Preservative                    |
|   | 5.0   | 1,2-propylene glycol| Propylene Glycol                |
|   | 0.7   | Magnesium sulfate   | Magnesium Sulfate               |
|   | 48.20 | Water dem.          | Aqua dem.                       |

COMPARATIVE EXAMPLE 1

Emulsion B comprising 4% by weight of zinc oxide (sun protection factor 4)

|   | %     | Raw material        | INCI                            |
|---|-------|---------------------|---------------------------------|
| I | 6.00  | Chremophor ® WO7    | PEG-7 Hydrogenated Castor Oil   |
|   | 0.30  | Chremophor ® RH 410 | PEG-40 Hydrogenated Castor Oil  |
|   | 2.00  | Elfacos ® ST9       | PEG-45/Dodecyl Glycol Copolymer |
|   | 2.00  | Elfacos ® C26       | Hydroxyoctacosanyl Hydroxystearate |
|   | 12.00 | Finsolv ® TN        | Alkyl Benzoate                  |
|   | 0.5   | Magnesium stearate  | Magnesium Stearate              |
|   | 0.5   | Aluminum stearate   | Aluminum Stearate               |
|   | 10.00 | Isopropyl myristate | Isopropyl Myristate             |
|   | 0.5   | Preservative        | Preservative                    |
|   | 5.0   | Witconol ® APM      | PPG-3 Myristyl Ether            |
|   | 4.0   | Zinc oxide          | Zinc Oxide                      |
| II| 0.3   | Preservative        | Preservative                    |
|   | 5.0   | 1,2-propylene glycol| Propylene Glycol                |
|   | 0.7   | Magnesium sulfate   | Magnesium Sulfate               |
|   | 51.20 | Water dem.          | Aqua dem.                       |

COMPARATIVE EXAMPLE 2

Emulsion C comprising 3% by weight of Uvinul® T150 (sun protection factor 9)

|   | %     | Raw material        | INCI                            |
|---|-------|---------------------|---------------------------------|
| I | 6.00  | Chremophor ® WO7    | PEG-7 Hydrogenated Castor Oil   |
|   | 0.30  | Chremophor ® RH 410 | PEG-40 Hydrogenated Castor Oil  |
|   | 2.00  | Elfacos ® ST9       | PEG-45/Dodecyl Glycol Copolymer |
|   | 2.00  | Elfacos ® C26       | Hydroxyoctacosanyl Hydroxystearate |
|   | 12.00 | Finsolv ® TN        | Alkyl Benzoate                  |
|   | 0.5   | Magnesium stearate  | Magnesium Stearate              |
|   | 0.5   | Aluminum stearate   | Aluminum Stearate               |
|   | 10.00 | Isopropyl myristate | Isopropyl Myristate             |
|   | 3.00  | Uvinul ® T150       | Octyl Triazone                  |
|   | 0.5   | Preservative        | Preservative                    |
|   | 5.0   | Witcono ® APM       | PPG-3 Myristyl Ether            |
| II| 0.3   | Preservative        | Preservative                    |
|   | 5.0   | 1,2-propylene glycol| Propylene Glycol                |
|   | 0.7   | Magnesium sulfate   | Magnesium Sulfate               |
|   | 52.20 | Water dem.          | Agua dem.                       |

COMPARATIVE EXAMPLE 3

Emulsion D comprising 3% by weight of Uvinul® T150 and 4% by weight of Titanium dioxide (sun protection factor 11)

|   | %     | Raw material        | INCI                            |
|---|-------|---------------------|---------------------------------|
| I | 6.00  | Chremophor ® WO7    | PEG-7 Hydrogenated Castor Oil   |
|   | 0.30  | Chremophor ® RH 410 | PEG-40 Hydrogenated Castor Oil  |
|   | 2.00  | Elfacos ® ST9       | PEG-45/Dodecyl Glycol Copolymer |
|   | 2.00  | Elfacos ® C26       | Hydroxyoctacosanyl Hydroxystearate |
|   | 12.00 | Finsolv ® TN        | Alkyl Benzoate                  |
|   | 0.5   | Magnesium stearate  | Magnesium Stearate              |
|   | 0.5   | Aluminum stearate   | Aluminum Stearate               |
|   | 10.00 | Isopropyl myristate | Isopropyl Myristate             |
|   | 3.00  | Uvinul ® T150       | Octyl Triazone                  |
|   | 0.5   | Preservative        | Preservative                    |
|   | 5.0   | Witconol ® APM      | PPG-3 Myristyl Ether            |
|   | 4.0   | Tioveil ® MOTG      | Titanium Dioxide                |
| II| 0.3   | Preservative        | Preservative                    |
|   | 5.0   | 1,2-propylene glycol| Propylene Glycol                |
|   | 0.7   | Magnesium sulfate   | Magnesium Sulfate               |
|   | 48.20 | Water dem.          | Agua dem.                       |

COMPARATIVE EXAMPLE 4

Emulsion E comprising 4% by weight of titanium dioxide (sun protection factor 6)

|   | %     | Raw material        | INCI                            |
|---|-------|---------------------|---------------------------------|
| I | 6.00  | Chremophor ® WO7    | PEG-7 Hydrogenated Castor Oil   |
|   | 0.30  | Chremophor ® RH 410 | PEG-40 Hydrogenated Castor Oil  |
|   | 2.00  | Elfacos ® ST9       | PEG-45/Dodecyl Glycol Copolymer |
|   | 2.00  | Elfacos ® C26       | Hydroxyoctacosanyl Hydroxystearate |
|   | 12.00 | Finsolv ® TN        | Alkyl Benzoate                  |

-continued

| % | Raw material | INCI |
|---|---|---|
| 0.5 | Magnesium stearate | Magnesium Stearate |
| 0.5 | Aluminum stearate | Aluminum Stearate |
| 10.00 | Isopropyl myristate | Isopropyl Myristate |
| 0.5 | Preservative | Preservative |
| 5.0 | Witconol ® APM | PPG-3 Myristyl Ether |
| 4.0 | Tioveil ® MOTG | Titanium Dioxide |
| II 0.3 | Preservative | Preservative |
| 5.0 | 1,2-propylene glycol | Propylene Glycol |
| 0.7 | Magnesium sulfate | Magnesium Sulfate |
| 51.20 | Water dem. | Aqua dem. |

We claim:

1. A cosmetic or pharmaceutical preparation comprising a) from 0.1 to 10% by weight of one or more 1,3,5-triazine derivatives of the formula I,

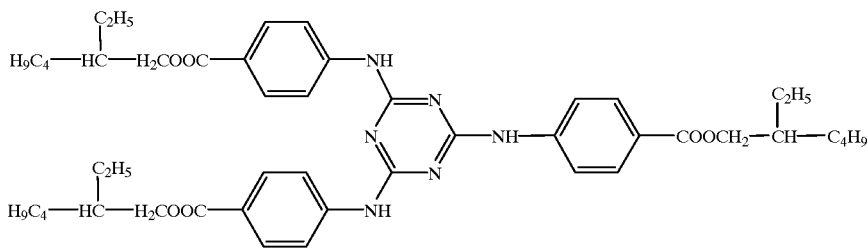

in which the substituents independently of one another have the following meanings:
$R^1$ to $R^3$
are $C_1$–$C_{20}$-alkyl, aryl, heteroaryl, optionally substituted;
X is O, $NR^4$;
$R^4$ is hydrogen, $C_1$–$C_{20}$-alkyl, aryl, heteroaryl, optionally substituted, and b) from 0.1 to 15% by weight of zinc oxide.

2. A cosmetic or pharmaceutical preparation as defined in claim 1, comprising a) from 1 to 8% by weight of one or more 1,3,5-triazine derivatives of the formula I in which the substituents independently of one another have the following meanings:
$R^1$ to $R^3$
are $C_4$–$C_8$-alkyl;
X is O, $NR^4$;
$R^4$ is hydrogen, $C_4$–$C_8$-alkyl, and b) from 0.1 to 10% by weight of zinc oxide.

3. A cosmetic or pharmaceutical preparation as defined in claim 1, comprising a) from 2 to 6% by weight of 2,4,6-trianilino-p-(carbo-2'-ethylhexyl-1'-oxy)-1,3,5-triazine of the formula Ia and b) from 2 to 8% by weight of zinc oxide.

4. A cosmetic or pharmaceutical preparation as defined in claim 1, comprising a) from 2.5 to 5% by weight of 2,4,6-trianilino-p-(carbo-2'-ethylhexyl-1'-oxy)-1,3,5-triazine of the formula Ia and b) from 3.5 to 6% by weight of zinc oxide.

5. A cosmetic or pharmaceutical preparation as defined in claim 1 having a sun protection factor of >14.

6. A cosmetic or pharmaceutical preparation as defined in claim 1 having a sun protection factor of >25.

7. A method of protecting human skin or human hair from solar rays which comprises: applying to the skin or hair a cosmetic or pharmaceutical composition containing an effective amount of a preparation as defined in claim 1.

* * * * *